US006440621B1

(12) United States Patent
Sutton et al.

(10) Patent No.: US 6,440,621 B1
(45) Date of Patent: Aug. 27, 2002

(54) METHOD OF DETECTING FILM DEFECTS USING CHEMICAL EXPOSURE OF PHOTORESIST FILMS

(75) Inventors: Daniel E. Sutton; Christopher H. Lansford, both of Austin, TX (US)

(73) Assignee: Advanced Micro Devices, Inc., Sunnyvale, CA (US)

(*) Notice: Subject to any disclaimer, the term of this patent is extended or adjusted under 35 U.S.C. 154(b) by 50 days.

(21) Appl. No.: 09/703,081

(22) Filed: Oct. 31, 2000

(51) Int. Cl.[7] .............................. G03F 9/00; G03C 5/00; G06K 9/00
(52) U.S. Cl. ..................... 430/30; 430/330; 382/149
(58) Field of Search .................... 430/30, 330; 382/149

(56) References Cited

PUBLICATIONS

P.E. Wagner and M. Kerker; Brownian coagulation of aerosols in rarefied gases; The Journal of Chemical Physics; vol. 66, No. 2; pp. 638–646; Jan. 15, 1977.

Ganesan Narsimhan et al.; Dissociation Kinetics of Doublets of Aerosol Particles; Journal of Colloid and Interface Science; vol. 116, No. 1; pp. 278–287; Mar. 1987.

L. David Pratt; Photoresist aerosol particle formation during spin–coating; Proceedings SPIE–The International Society of Optical Engineering; vol. 1262; pp. 170–179; Mar. 5–6, 1990.

Linda M. Bond et al.; Using Laser Surface Scanning and Bare Wafer Review to Diagnose Photolithography Track Developer Process Induced Defect Issues; SPIE 24th International Symposium on Microlithography; pp. 1–9; 1999.

John Sturtevant et al.; Substrate Contamination Effects in the Processing of Chemically Amplified DUV Photoresists; Proceedings SPIE–The International Society of Optical Engineering; pp. 770–780; May 1994.

Hiroshi Ito; Deep–UV resists: Evolution and Status; Solid State Technology; 164–166, 168, 170 and 173; Jul. 1996.

Khoi Phan et al.; Efficient and Cost Effective Photo Defect Monitoring; Proceedings SPIE–The International Society of Optical Engineering; vol. 3332; pp. 709–713; Feb. 23–25, 1998.

Linda M. Bond et al.; Use of Multiple Lithography Monitors in a Defect Control strategy for High Volume Manufacturing; 10th Annual IEEE/SEMI Advanced Semiconductor Manufacturing Conference and Workshop; all; 1999.

*Primary Examiner*—Christopher G. Young
(74) *Attorney, Agent, or Firm*—Timothy M. Honeycutt

(57) ABSTRACT

Various methods of inspecting a semiconductor workpiece for defects are provided. In one aspect, a method of inspecting a surface of a semiconductor workpiece for defects is provided that includes applying a negative-tone photoresist film to the surface and baking the negative-tone photoresist film to release solvent therefrom and to facilitate release of catalyzing substances held by the defects into the negative-tone photoresist film. The catalyzing substances react chemically with at least one moiety of the photoresist film to thereby lower the solubility of one or more portions of the negative-tone photoresist film in a developer. The negative-tone photoresist film is developed with the developer and the surface is inspected for the portions of the negative-tone photoresist film remaining after the developing process. The remaining portions of the negative-tone photoresist film are indicative of the locations of the defects.

25 Claims, 6 Drawing Sheets

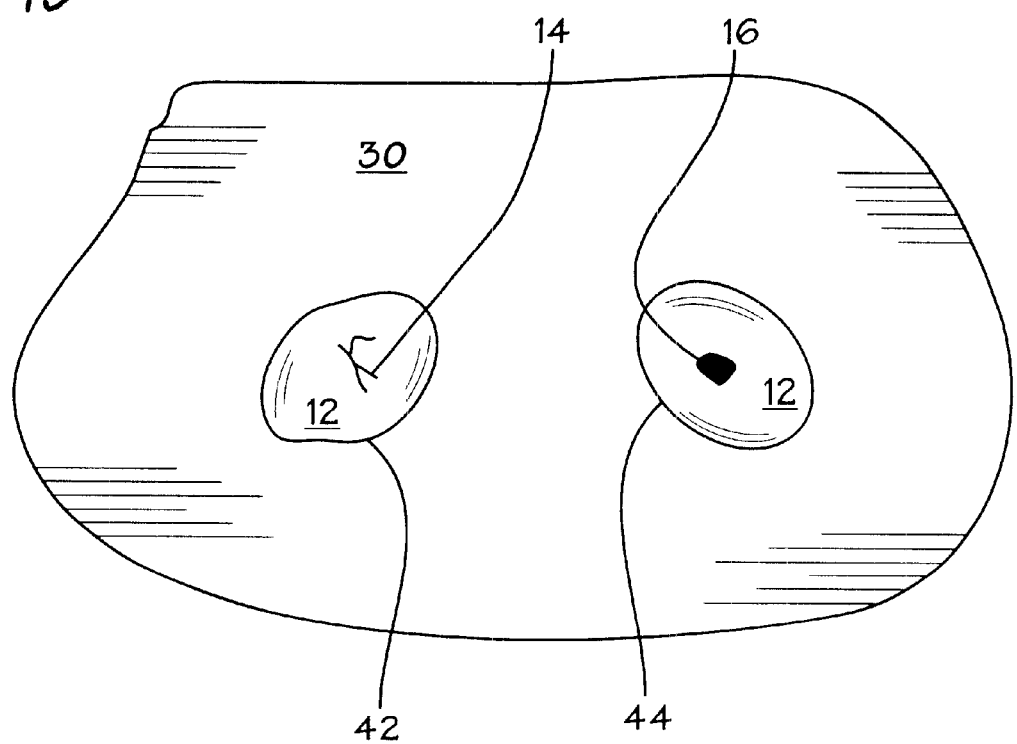

METHOD OF DETECTING FILM DEFECTS USING CHEMICAL EXPOSURE OF PHOTORESIST FILMS

BACKGROUND OF THE INVENTION

1. Field of the Invention

This invention relates generally to semiconductor processing, and more particularly to methods of inspecting semiconductor workpieces for surface defects using chemical exposure of resist films.

2. Description of the Related Art

Large scale integrated circuits now routinely contain millions of individual transistors and other electronic components. Most of the interconnections for the numerous individual components are provided via one or more metallization layers that serve as global interconnect levels. Each metallization layer is ordinarily deposited on the substrate of the integrated circuit as a single continuous layer that is thereafter patterned lithographically and etched to remove metal from areas where metal lines are not required.

In addition to the one or more metallization layers, modern integrated circuits also incorporate numerous routing-restricted interconnect levels commonly known as local interconnects and contacts. Local interconnects and contacts are used for short metallization runs such as those that locally interconnect gates and drains in NMOS and CMOS circuits and those that connect a given metallization layer to a particular structure in the integrated circuit.

A method frequently employed to form contact structures involves a damascene process in which the substrate containing the integrated circuit is coated with a layer of dielectric material that is lithographically patterned and etched to form contacts or vias in the dielectric layer where the contact structures will be formed. Thereafter, the contact material, or materials if a laminate structure is desired, is deposited over the dielectric layer. The goal of the deposition process is to fill the vias as completely as possible. Finally, a planarization process is performed to remove the excess conducting material from the dielectric layer and leave only the filled vias.

A variety of defects may arise during processing of interlevel dielectric and metallization layers. For example, portions of the upper surface of the interlevel dielectric layer may crack as a result of differential thermal stresses or rip-out during chemical-mechanical-polishing "CMP". In addition, contaminant particles may be left or deposited on the interlevel dielectric layer following CMP of the bulk-deposited metallization film. In either case, the defect can interfere with subsequent lithography processing on the interlevel dielectric layer, via etching or conductor deposition. Moreover, the problem is not limited to interlevel dielectric-contact formation. Indeed, the successful application of stacked films often requires a relatively pristine underlying surface upon which each successive layer is formed. However, the presence of defects in the surface of an underlying layer may cause the overlying film to later delaminate and lead to device failure.

Therefore, accurate, reliable and early defect inspection is vital to successful semiconductor fabrication. It is desirable to be able to identify film surface defects as early in a given process flow as possible since continued production processing of wafers that will ultimately have to be scrapped or reworked represents waste in terms of both fab time and material. As an example, undetected surface defects in an interlevel dielectric layer may result in poor contact lithography or etching. In such circumstances, the time and material involved in the contact lithography, e.g., the photoresist application, exposure, development, and contact etch will be wasted.

Currently, inspection for surface defects is performed with various types of scanning tools. Some of these employ optical scanning, while others utilize laser scanning. Many conventional contact defect scanning techniques utilize die-to-die comparison, although die-to-database comparing is also sometimes used.

A limitation associated with conventional surface defect inspection is tool sensitivity. Many types of defects are too small for the inspection tool to resolve. Other types may elude detection because their geometries mimic patterned features in the film. Still others may go undetected because they occur relatively infrequently across the surface of a given film. As a time savings measure, many metrology tools are set up to examine only certain sample portions of a given film. Thus, defects capable of causing device failure may pass inspection if they do not happen to fall within the designated sample portions of the film.

Another limitation associated with some conventional defect inspection methods is destruction of the scanned surface. Techniques such as transmission electron microscopy and time of flight secondary ion beam spectroscopy can identify certain kinds of defects, but also result in the destruction of the scanned structure.

The present invention is directed to overcoming or reducing the effects of one or more of the foregoing disadvantages.

SUMMARY OF THE INVENTION

In accordance with one aspect of the present invention, a method of inspecting a surface of a semiconductor workpiece for defects is provided that includes applying a negative-tone photoresist film to the surface and baking the negative-tone photoresist film to release solvent therefrom and to facilitate release of catalyzing substances held by the defects into the negative-tone photoresist film. The catalyzing substances react chemically with at least one moiety of the photoresist film to thereby lower the solubility of one or more portions of the negative-tone photoresist film in a developer. The negative-tone photoresist film is developed with the developer and the surface is inspected for the portions of the negative-tone photoresist film remaining after the developing process. The remaining portions of the negative-tone photoresist film are indicative of the locations of the defects.

In accordance with another aspect of the present invention, a method of inspecting a surface of a semiconductor workpiece for defects is provided that includes applying a positive-tone photoresist film to the surface and baking the positive-tone photoresist film to release solvent therefrom and to facilitate release of catalyzing substances held by the defects into the positive-tone photoresist film. The catalyzing substances react chemically with at least one moiety of the photoresist film to thereby increase the solubility of one or more portions of the positive-tone photoresist film. The positive-tone photoresist film is developed with the developer and the surface is inspected for the dissolved portions of the positive-tone photoresist film appearing after the developing process. The dissolved portions of the positive-tone photoresist film are indicative of the locations of the defects.

In accordance with another aspect of the present invention, a method of inspecting a dielectric film on a semiconductor workpiece for defects is provided that includes applying a photoresist primer to the dielectric film and applying a negative-tone photoresist film to the dielectric film. The negative-tone photoresist film has actinic sensitivity to deep ultraviolet radiation. The negative-tone photoresist film is baked to release solvent therefrom and to facilitate release of acidic substances held by the defects into the negative-tone photoresist film. The acidic substances react chemically with and thereby lower the solubility of one or more portions of the negative-tone photoresist film. The negative-tone photoresist film is developed with the developer and the dielectric film is inspected for the portions of the negative-tone photoresist film remaining after the developing process. The remaining portions of the negative-tone photoresist film are indicative of the locations of the defects.

BRIEF DESCRIPTION OF THE DRAWINGS

The foregoing and other advantages of the invention will become apparent upon reading the following detailed description and upon reference to the drawings in which:

FIGS. 9–13 are cross-sectional views of the workpiece depicting an alternate exemplary method of inspecting for defects thereon utilizing positive-tone photoresist in accordance with the present invention.

DETAILED DESCRIPTION OF SPECIFIC EMBODIMENTS

Figure 1:
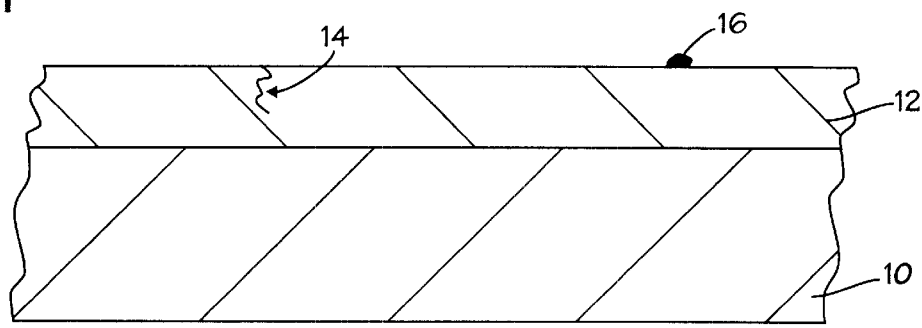
FIG. 1 is a cross-sectional view of a small portion of a semiconductor workpiece that includes two representative film defects in accordance with the present invention.

In the drawings described below, reference numerals are generally repeated where identical elements appear in more than one figure. An exemplary method of inspecting a semiconductor workpiece 10 for defects may be understood by referring now to FIGS. 1–8 and initially to FIG. 1. FIG. 1 depicts a cross-sectional view of a small portion of the a semiconductor workpiece 10 upon which a semiconductor processing film 12 is formed. The workpiece 10 may be a semiconductor wafer or other type of substrate used in circuit fabrication and may be composed of silicon, silicon-on-insulator or other widely used substrate materials. The processing film 12 may be any of a variety of films used in semiconductor processing, such as, for example, oxide, silicon nitride, silicon oxynitride, polycrystalline or amorphous silicon or the like. For the purposes of the present illustration, the film 12 is an oxide film of the type used as interlevel dielectric layers.

As the skilled artisan will appreciate, the myriad of processing steps used to form, shape and remove various semiconductor processing films can lead to the introduction of a wide range of defects in a given film. Two such defects 14 and 16 are depicted in FIG. 1 for the purpose of the present illustration. The defect 14 is a crack or fissure in the film 12 and the defect 16 is a contaminant particle. The fissure 14 may be formed through a variety of mechanisms, such as, for example, CMP rip-out, thermal stress cracking, or perturbations during chemical vapor deposition to name just a few. The particle 16 may consist of a metal particle left over from a prior metallization, CMP or other step. For the purpose of the present illustration, the particle 16 is composed of aluminum.

Solvent cleaning steps are frequently performed in semiconductor processing following CMP, CVD and etching processes to name just a few. In many cases, the solvent process involves cleansing the surface in question using ammonium hydroxide, peroxide and water solutions or other solutions that contain acid or base compounds. Experiment has shown that the defects 14 and 16 may act as repositories for substances capable of catalyzing one or moieties present in photoresist materials and thereby changing the solubility of photoresist materials in a developer solution. The fissure defect 14 acts as a repository in the usual sense, that is, as a storage vessel for such catalyzing substances. The aluminum particle 16 functions as a repository through a different mechanism. Exposing the aluminum particle 16 to a hydroxide solution will result in the formation of an aluminum hydroxide ($Al(OH)_3$) particle or at least an aluminum particle coated with a film of aluminum hydroxide. Thereafter, the aluminum hydroxide may catalyze one or more of the moieties of a later-applied photoresist film.

Figure 2:
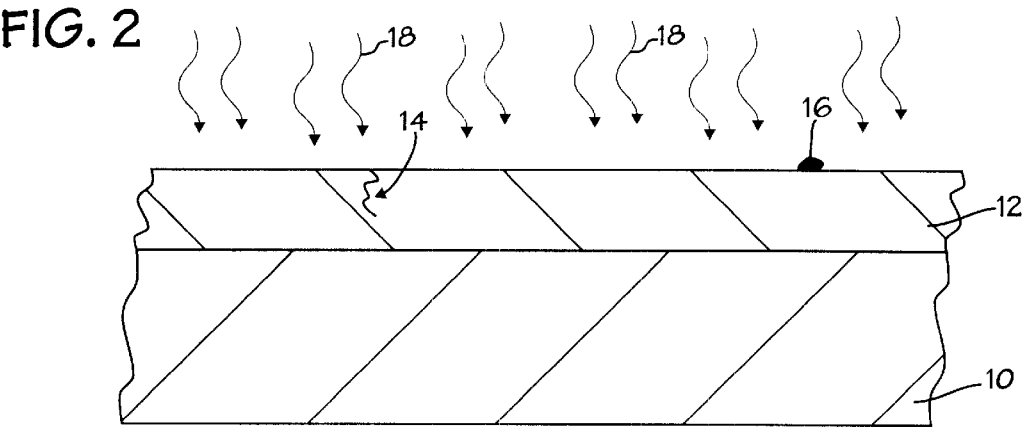
FIG. 2 is a cross-sectional view like FIG. 1 depicting photoresist priming of a semiconductor processing film on the workpiece in accordance with the present invention.

Experiment has shown that the propensity of the defects 14 and 16 to store, either physically or chemically, substances capable of catalyzing one or moieties of photoresist materials may be used as a means of detecting the presence of the defects 14 and 16. The process will now be described. Referring now to FIG. 2, the film 12 is initially subjected to a dehydration bake for about 30 to 60 seconds at about 100 to 180° C. The heating ambient may be ambient air at atmospheric pressure. Priming of the surface 12 may be desirable to facilitate photoresist adhesion, particularly if the film 12 is composed of oxide. Priming may be combined with the dehydration bake. During the heating cycle, the film 12 may be primed with a vapor 18 such as hexamethyldisilazane, DEATS, a combination of the two or other well known photoresist primers. As an alternative to vapor priming, the primer 18 may be applied by spin coating.

Figure 3:
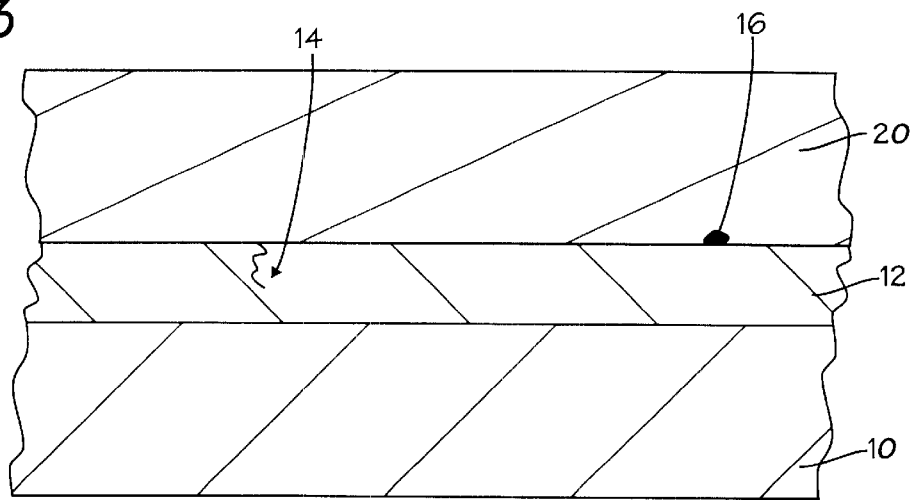
FIG. 3 is a cross-sectional view like FIG. 2 depicting application of a negative-tone photoresist film on the semiconductor processing film in accordance with the present invention.

Referring now to FIG. 3, a negative-tone photoresist film 20 is applied over the film 12. The negative tone resist film 20 is advantageously composed of a matrix, a sensitizer consisting of one or more photo-acid generator(s), and a solvent. Any catalyzing substances held by the defects 14 and 16 will react chemically with one or more moieties of the resist 20 to produce an effective exposure of the portions of the resist film 20 in the vicinity of the defects 14 and 16. As used herein, the term "catalyzing substances" is intended to mean substances capable of reacting with moieties of the photoresist 20 so that the solubility of the photoresist 20 in a developer is either decreased, as in the case of negative-tone resist, or increased, as in the case of positive-tone resist.

Experiment has identified aluminum hydroxide as one such catalyzing substance. Solubility change in the resist film 20 is thought to be the result of chemical activation of photo-acid generators present in the photoresist 20 by the aluminum hydroxide from the defect 16. Regardless of the specific mechanism, the quasi-exposed portions of the resist film 20 will remain after development as conspicuous mounds or mesas of resist that may be easily detected using semiconductor inspection tools.

The variety of negative tone resist used to lay down the film 20 is largely a matter of design discretion. Experiment has shown that photoresist materials with actinic sensitivity to deep ultraviolet radiation provide excellent reactivity with catalyzing substances, such as acids and metal hydroxides, held by the defects 14 and 16. The particular type of negative tone resist used to lay down the film 20 is largely a matter of design discretion. In an exemplary embodiment, a photoresist that has actinic sensitivity to deep ultraviolet radiation, such as a Shipley® UVN® 30 resist, is applied to a thickness of about 8,000to 12,000 Å using about a 2 to 5 ml volume for a 200 mm diameter workpiece 10. The photoresist film 20 may be applied using spin coating at about 1000 to 4000 rpm. Again, these particular parameters will depend upon the size of the workpiece 10 and the type of photoresist material used.

If desired, a solvent pre-wet process may be performed just prior to application of the resist film 20 in order to overcome the surface energy of the primed surface of the film 12. A variety of well known solvent pre-wet solvents may be used. For example, a mixture of ethyl-lactate and 4-methyl-2-pentanone may be dispensed on the primed film 20 and spun off at a high spin speed, such as at about 5,000 to 10,000 rpm. As the pre-wet solvents are evaporating from the film 12, the resist film 20 is applied using the aforementioned techniques.

Figure 4:
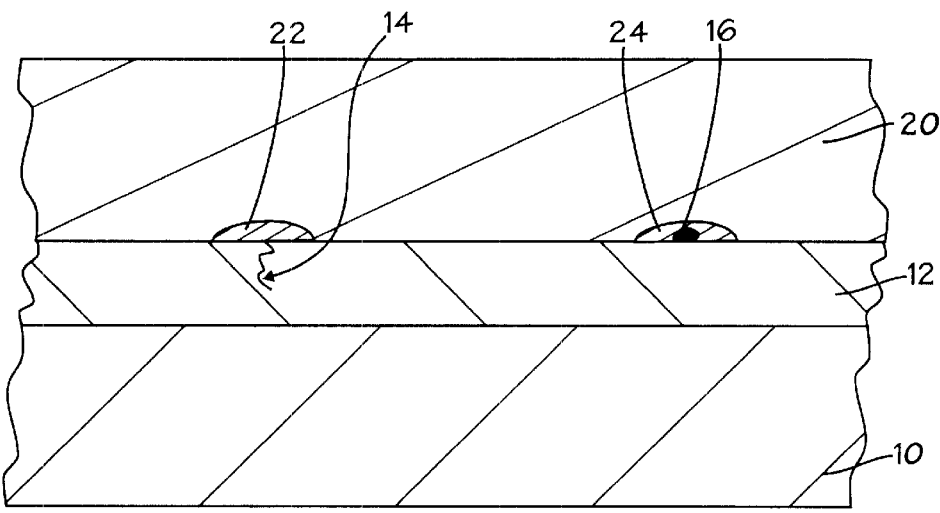
FIG. 4 is a cross-sectional view like FIG. 3 depicting initial formation of quasi-exposed regions in the photoresist film in accordance with the present invention.

Referring now to FIG. 4, it is anticipated that shortly after application of the resist film 20, small regions of quasi-exposed resist material 22 and 24 will form over the defects 14 and 16. The term "quasi-exposed" denotes that the regions 22 and 24 have undergone the solubility-altering chemical reaction(s) that are phenomenologically like those produced photochemically through exposure to actinic radiation. The solubility of the quasi-exposed regions 22 and 24 in appropriate developer solvents is lowered well below the solubility of the surrounding resist film 20 in the same general way that the solubility of negative tone resist is lowered by exposure to actinic radiation.

Figure 5:
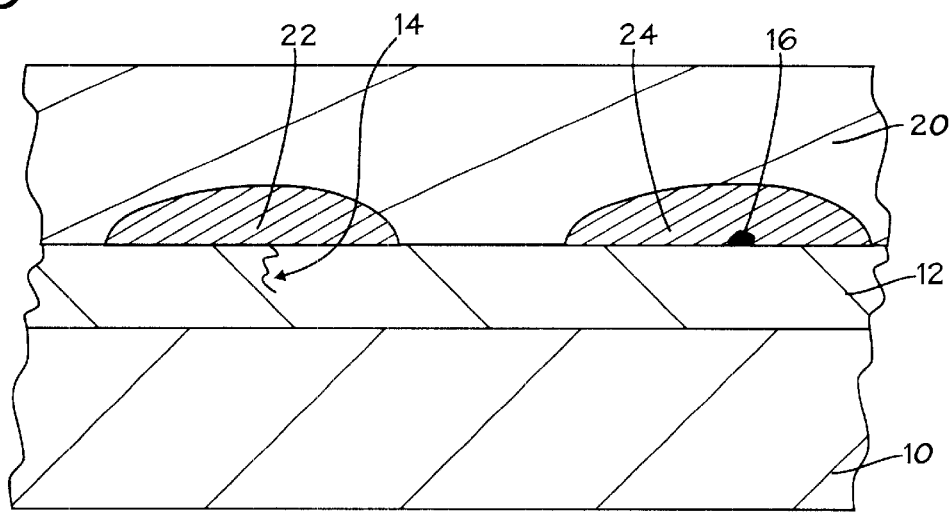
FIG. 5 is a cross-sectional view like FIG. 4 depicting a bake of the workpiece in accordance with the present invention.

Referring now to FIG. 5, the workpiece 10 is subjected to a double bake process. The goal of the bake process is two-fold. In an exemplary embodiment, a first bake is performed to liberate solvent from the resist film 20 and the second bake is performed largely to facilitate release of the catalyzing substances held by the defects 14 and 16 into the resist film 20. The goal is to enlarge the quasi-exposed regions 22 and 24 so that they may be easily detected during subsequent inspection. In an exemplary embodiment, the workpiece 10 is heated to about 90 to 110° C. for about 45 to 90 seconds at atmospheric pressure. The heating may be accomplished on a hot plate with about a 1 mm plate-to-substrate separation. Thereafter, the workpiece 10 is heated to about 90 to 110° C. for about 45 to 300 seconds. Optionally, a single heating step may be performed at about 90 to 110° C. for about 45 to 300 seconds.

Figure 6:
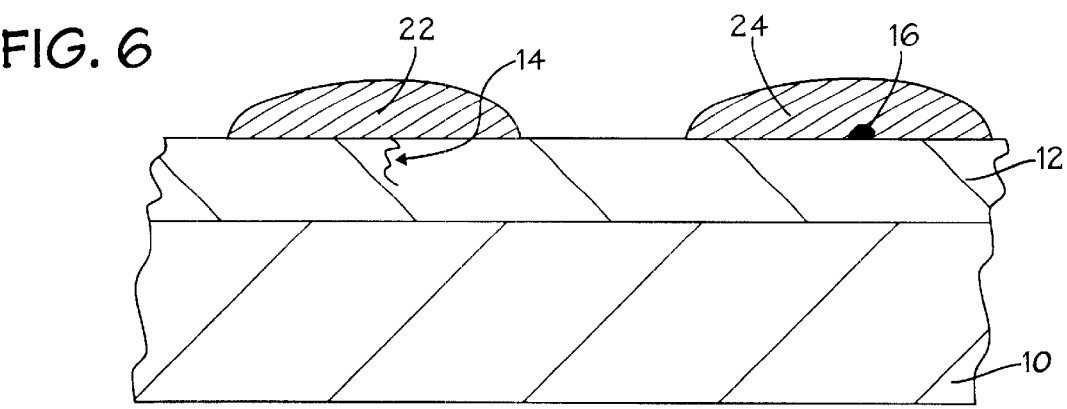
FIG. 6 is a cross-sectional view like FIG. 5 depicting development of the photoresist film in accordance with the present invention.
Figure 7:
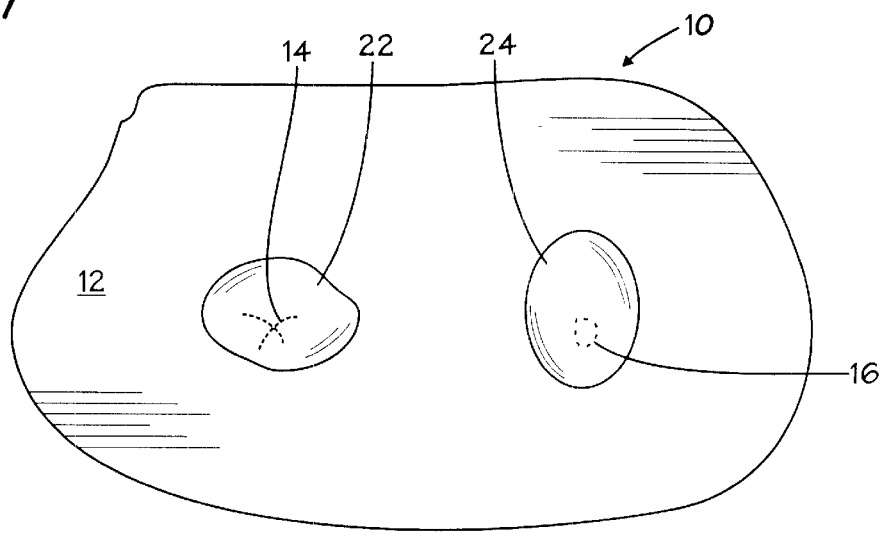
FIG. 7 is a plan view of the workpiece after development of the photoresist film in accordance with the present invention.

Referring now also to FIG. 6, the photoresist film 20 is developed. The developing process dissolves the otherwise unexposed resist film 20 leaving only the quasi-exposed mounds or mesas 22 and 24. An overhead view of the semiconductor processing film 12 and the quasi-exposed mesas 22 and 24 following the development step is shown in FIG. 7. The appropriate development process will depend upon the type of resist material involved. In an exemplary embodiment, the resist film 20 may be exposed to solution of 2.38% (by volume) tetra-methyl-ammonium-hydroxide in water. A multi-stream applicator head may be used with rotation of the semiconductor workpiece 10. The developer solution may be allowed to puddle for about 30 to 60 seconds. Thereafter, a deionized water rinse may be performed on the workpiece 10 for about 10 to 30 seconds, again using a multi-stream applicator with rotation of the workpiece 10.

Figure 8:
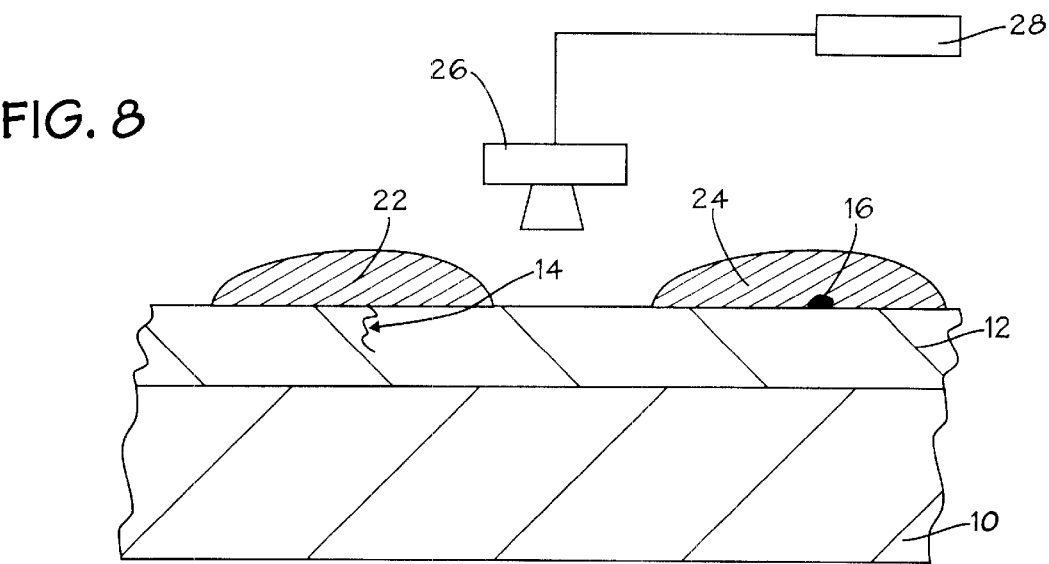
FIG. 8 is a cross-sectional view like FIG. 5 depicting inspection of the semiconductor processing film in accordance with the present invention.

As shown in FIG. 8, the workpiece 10 may be inspected for the presence of the conspicuous mesas 22 and 24. An inspection tool 26 may be used that is provided with or otherwise connected to a computing device 28 that provides data acquisition, control and database storage functions to name just a few. The inspection tool 20 may be any of a variety of inspection tools used to inspect semiconductor workpieces, such as, for example, optical or scanning electron microscopes, laser scattering tools, pattern comparators, dark field and bright field illumination tools to name just a few. If desired, the film 12 may be compared to a substantially identical film that has a known topography in order to facilitate discrimination of the mesas 22 and 24 from other features on the film 12. For example, die-to-die or die-to-database comparison may be used.

Although aluminum hydroxide has been identified as one source of resist catalyzing reactions, experiment has shown that the effect is exhibited by other metals. In one experiment droplets of a stock solution containing 10 $\mu$g/ml each of beryllium, bismuth, cerium, cobalt, indium, magnesium, nickel, lead and uranium in 2% nitric acid (by volume) was diluted down to about 1.0 mM. Droplets of this solution were applied to an oxide coated test wafer for about 2 seconds. The drops were rinsed away with water and isopropyl alcohol, leaving behind only a microscopic residue where the drops had been. A negative-tone photoresist film was thereafter baked, developed and inspected. Resist bumps or mesas remained where the droplets had been applied. A control run using just 2% nitric acid did not produce resist bumps. In another run, similar resist bumps were obtained using a stock solution of 10 $\mu$g/ml each of boron, germanium, molybdenum, niobium, phosphorus, rhenium, sulphur, silicon, tantalum, titanium, tungsten and zirconium in water. Still another run produced similar results using 10 $\mu$g/ml each of silver, aluminum, arsenic, barium, beryllium, bismuth, calcium, cadmium, cobalt, chromium, cesium, cerium, copper, iron, gallium, indium, potassium, lithium, magnesium, manganese, sodium, nickel, lead, rubidium, cerium, selenium, strontium, thallium, uranium, and vanadium, and zinc in 5% nitric acid by volume.

Figure 9:
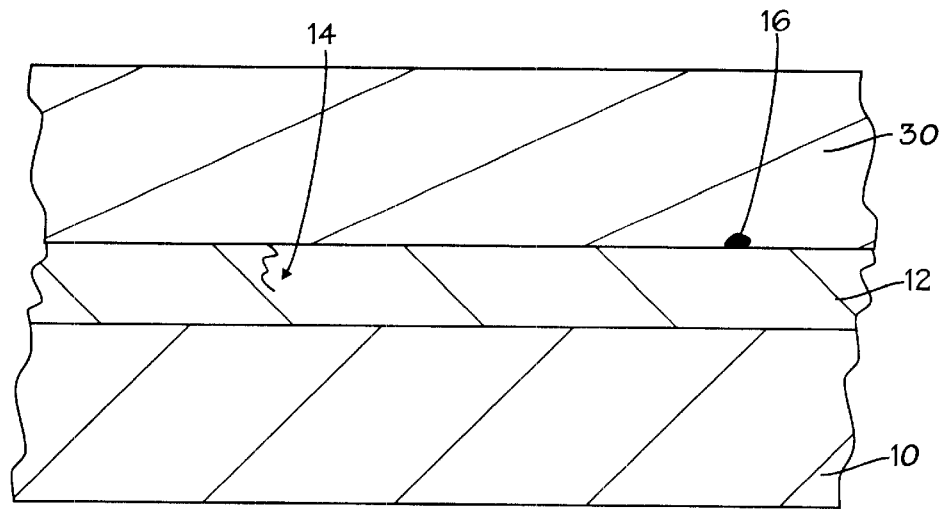
Figure 10:
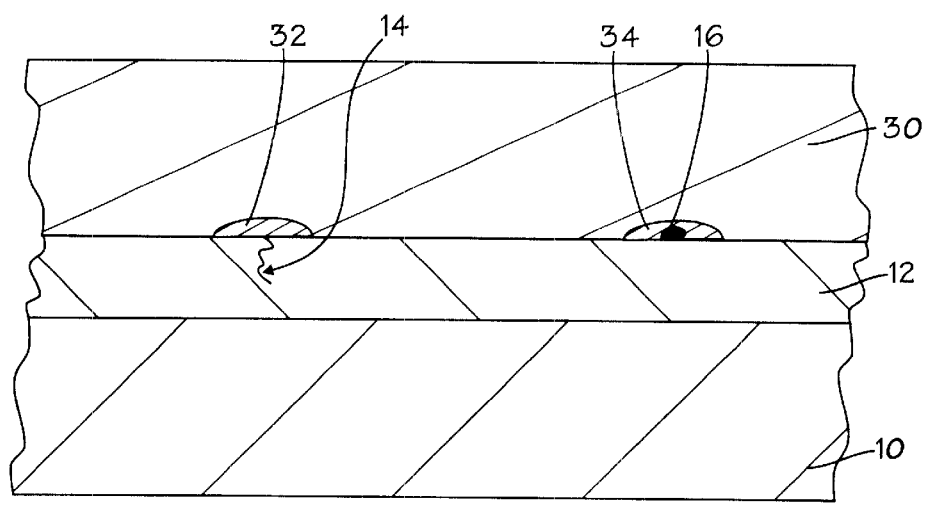

In the embodiment described above in conjunction with FIGS. 1–8, a negative tone resist film is used to flag the defects 14 and 16 in the film 12. However, a positive tone resist may be used in lieu of negative tone resist. This alternative embodiment may be understood by referring now to FIGS. 9–13 and initially to FIG. 9. The film 12 may be initially primed as described above in conjunction with FIG. 2. Thereafter, a positive tone resist film 30 is applied to the film 12. Again, the resist 30 will consist of a matrix, a sensitizer and a solvent. As with the foregoing illustrative embodiment, any catalyzing substances held by the defects 14 and 16 will react chemically with one or more moieties of the resist 30 to produce an effective exposure of the portions of the resist film 30 in the vicinity of the defects 14 and 16. The type of positive-tone resist used to form the film 30 is largely a matter of design discretion. In an exemplary embodiment, a photoresist that has actinic sensitivity to deep ultraviolet radiation, such as a Shipley® UV110 resist, is applied to a thickness of about 4,000 to 10,000 Å using the techniques described above for the negative tone resist.

Figure 11:
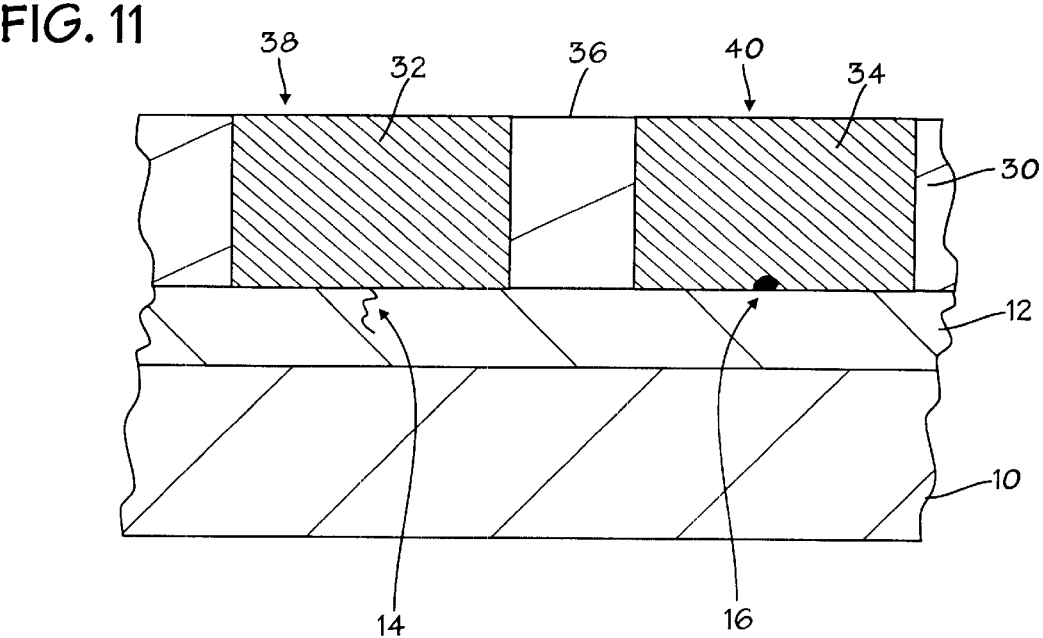

Referring now to FIG. 10, it is again anticipated that diffusion of the stored catalyzing substances will produce a localized reaction with the positive resist film 30 and produce the formation of quasi-exposed regions 32 and 34 overlying the defects 14 and 16. The quasi-exposed regions 32 and 34 will have a much higher solubility in a developer solvent than the surrounding portions of the resist film 30. Note, however, that at this stage of the process, a development step would not result in the dissolution of the regions 30 and 32 in a developer solution since the bulk portion of the resist film 30 overlying the regions 32 and 34 will still exhibit low solubility in the developer solution. Accordingly, and as depicted in FIG. 11, the workpiece 10 is subjected to a two stage baking process as generally described above. The goal of the bake process is not only to liberate most of the solvent from the resist film 30 but also to ensure that the reaction between the trapped catalyzing substances in or on the defects 14 and 16 precedes upward to the upper surface 36 of the resist film 30. In this way, the upper surfaces 38 and 40 of the respective quasi-exposed regions 32 and 34 may be directly exposed to the developer solution so that dissolution thereof may take place.

Figure 12:
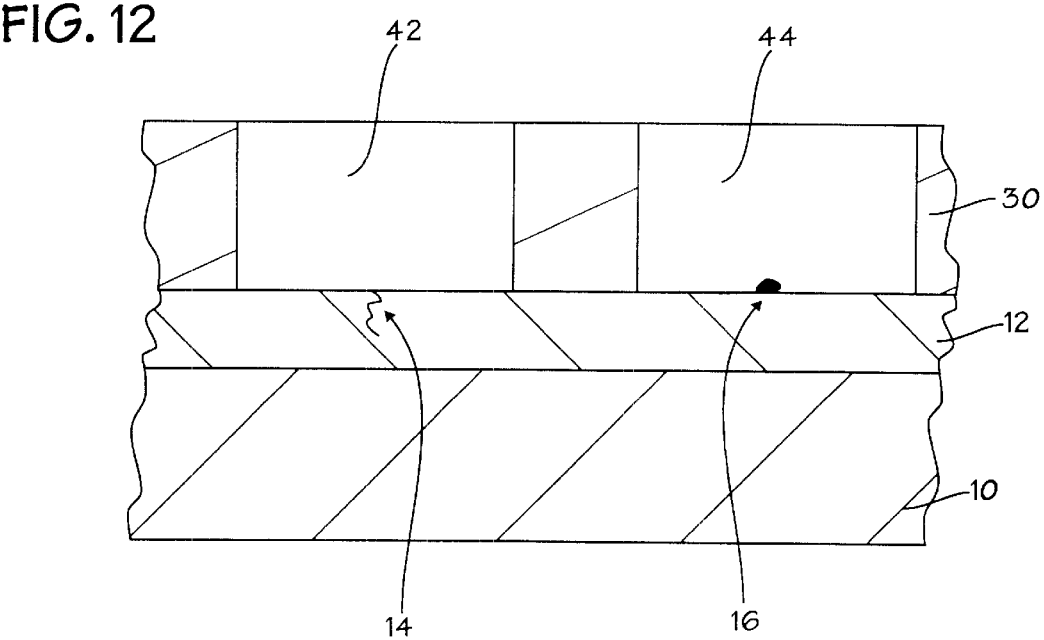

Referring now also to FIG. 12, the workpiece 10 is subjected to a developing process that dissolves the soluble quasi-exposed regions 32 and 34 that leaves relatively large and conspicuous holes 42 and 44 in the resist film 30. Again, the development process used will depend in large part on design discretion and the particular type of resist material used for the photoresist film 30. In an exemplary embodiment, an alkaline solution of either KOH or NaOH with a normality of about 0.5 may be used following the puddling procedure outlined above.

An overhead view of the resist film 30 following development is shown in FIG. 13. The conspicuous holes 40 and 42 in the resist film 30 may be readily detected using the inspection techniques described above in conjunction with FIG. 8. Note that the development process and the corresponding formation of the holes 40 and 42 may actually expose the underlying defects 14 and 16 on or in the film 12 as shown.

The skilled artisan will appreciate that the methods in accordance with the present invention provide for the identification of the locations of various types of film defects using the chemical properties of photoresist materials. The techniques utilize chemical as opposed to photochemical reactions to flag the locations of the defects. The methods may be used on production wafers as the various process steps are non-destructive. Defects may be detected prior to a production resist, exposure and development processing, resulting in less waste in fabrication time and material. As the defect areas are flagged chemically as opposed to photochemically, exposure is not necessary. However, the method may be integrated into a production masking process by setting aside a portion of the production resist film for defect inspection. The reticle used to expose the production resist film would be provided with a large dark field that will prevent exposure of the portion of the film set aside for defect inspection. In this way, solubility changes in the set aside region would not be the result of actinic radiation.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A method of inspecting a surface of a semiconductor workpiece for defects, comprising:
   applying a negative-tone photoresist film to the surface;
   baking the negative-tone photoresist film to release solvent therefrom and to facilitate release of any catalyzing substances held by the defects into the negative-tone photoresist film, the catalyzing substances reacting chemically with the at least one moiety of the photoresist film to thereby lower the solubility of one or more portions of the negative-tone photoresist film in a developer;
   developing the negative-tone photoresist film with the developer; and
   inspecting the surface for the portions of the negative-tone photoresist film remaining after the developing process, the remaining portions of the negative-tone photoresist film being indicative of the locations of the defects.

2. The method of claim 1, comprising applying a photoresist primer to the surface.

3. The method of claim 2, wherein the application of the photoresist primer comprises vapor priming while baking the surface.

4. The method of claim 1, wherein the negative-tone photoresist film comprises a photoresist having actinic sensitivity to deep ultraviolet radiation.

5. The method of claim 1, wherein the application of the negative-tone photoresist film comprises spin coating the surface with negative-tone photoresist.

6. The method of claim 1, wherein the baking of the negative-tone photoresist film comprises performing a first bake to liberate most of the solvent therefrom followed by a second bake to facilitate release of the catalyzing substances.

7. The method of claim 1, wherein the inspection of the surface comprises comparing the surface with a substantially identical surface having a known topography.

8. The method of claim 7, wherein the substantially identical surface comprises another semiconductor workpiece.

9. The method of claim 7, wherein the substantially identical surface comprises an image retrieved from a database.

10. A method of inspecting a surface of a semiconductor workpiece for defects, comprising:
    applying a positive-tone photoresist film to the surface;
    baking the positive-tone photoresist film to release solvent therefrom and to facilitate release of any catalyzing substances held by the defects into the positive-tone photoresist film, the catalyzing substances reacting chemically with at least one moiety of the photoresist film to thereby increase the solubility of one or more portions of the positive-tone photoresist film in a developer;
    developing the positive-tone photoresist film with the developer; and
    inspecting the surface for the dissolved portions of the positive-tone photoresist film appearing after the developing process, the dissolved portions of the positive-tone photoresist film being indicative of the locations of the defects.

11. The method of claim 10, comprising applying a photoresist primer to the surface.

12. The method of claim 11, wherein the application of the photoresist primer comprises vapor priming while baking the surface.

13. The method of claim 10, wherein the positive-tone photoresist film comprises a photoresist having actinic sensitivity to deep ultraviolet radiation.

14. The method of claim 10, wherein the application of the positive-tone photoresist film comprises spin coating the surface with positive-tone photoresist.

15. The method of claim 10, wherein the baking of the positive-tone photoresist film comprises performing a first bake to liberate most of the solvent therefrom followed by a second bake to facilitate release of the acidic substances.

16. The method of claim 10, wherein the inspection of the surface comprises comparing the surface with a substantially identical surface having a known topography.

17. The method of claim 16, wherein the substantially identical surface comprises another semiconductor workpiece.

18. The method of claim 16, wherein the substantially identical surface comprises an image retrieved from a database.

19. A method of inspecting a dielectric film on a semiconductor workpiece for defects, comprising:

applying a photoresist primer to the dielectric film;

applying a negative-tone photoresist film to the dielectric film, the negative-tone photoresist film having actinic sensitivity to deep ultraviolet radiation;

baking the negative-tone photoresist film to release solvent therefrom and to facilitate release of catalyzing substances held by the defects into the negative-tone photoresist film, the catalyzing substances reacting chemically with at least one moiety of the photoresist film to thereby lower the solubility of one or more portions of the negative-tone photoresist film in a developer;

developing the negative-tone photoresist film with a developer; and inspecting the dielectric film for the portions of the negative-tone photoresist film remaining after the developing process, the remaining portions of the negative-tone photoresist film being indicative of the locations of the defects.

20. The method of claim 19, wherein the application of the photoresist primer comprises vapor priming while baking the semiconductor workpiece.

21. The method of claim 19, wherein the application of the negative-tone photoresist film comprises spin coating the dielectric film with negative-tone photoresist.

22. The method of claim 19, wherein the baking of the negative-tone photoresist film comprises performing a first bake to liberate most of the solvent therefrom followed by a second bake to facilitate release of the catalyzing substances.

23. The method of claim 19, wherein the inspection of the dielectric film comprises comparing the dielectric film with a substantially identical dielectric film having a known topography.

24. The method of claim 23, wherein the substantially identical dielectric film comprises another dielectric film on another semiconductor workpiece.

25. The method of claim 23, wherein the substantially identical dielectric film comprises an image of the substantially identical dielectric film retrieved from a database.

* * * * *